United States Patent
Scott et al.

(10) Patent No.: US 10,980,659 B2
(45) Date of Patent: Apr. 20, 2021

(54) HEAD POSITIONING AIDS FOR PREMATURE INFANTS

(71) Applicant: Tortle Products LLC, Greenwood Village, CO (US)

(72) Inventors: Jane Scott, Castle Rock, CO (US); Cameron Fitch, Franktown, CO (US); Brendan Fitch, Denver, CO (US)

(73) Assignee: Tortle Products LLC, Greenwood Village, CO (US)

( * ) Notice: Subject to any disclaimer, the term of this patent is extended or adjusted under 35 U.S.C. 154(b) by 0 days.

(21) Appl. No.: 14/312,594

(22) Filed: Jun. 23, 2014

(65) Prior Publication Data

US 2014/0373278 A1     Dec. 25, 2014

Related U.S. Application Data

(60) Provisional application No. 61/838,050, filed on Jun. 21, 2013, provisional application No. 61/930,898, filed on Jan. 23, 2014.

(51) Int. Cl.
| | |
|---|---|
| *A42B 1/22* | (2006.01) |
| *A42B 3/14* | (2006.01) |
| *A61F 5/37* | (2006.01) |
| *A61M 16/06* | (2006.01) |

(52) U.S. Cl.
CPC ....... *A61F 5/3707* (2013.01); *A61M 16/0683* (2013.01); *A61M 16/0672* (2014.02); *A61M 2240/00* (2013.01); *Y10T 29/49826* (2015.01)

(58) Field of Classification Search
CPC .......... A47D 13/08; A42B 1/045; A42B 1/22; A42B 1/24; A42B 1/208
See application file for complete search history.

(56) References Cited

U.S. PATENT DOCUMENTS

| | | | | | |
|---|---|---|---|---|---|
| 1,652,145 | A | * | 12/1927 | Lipschutz | A42B 1/22 2/195.3 |
| RE17,064 | E | * | 8/1928 | Fischer | A42B 1/22 2/173.5 |

(Continued)

FOREIGN PATENT DOCUMENTS

| | | |
|---|---|---|
| AU | 2010200884 A1 | 9/2011 |
| CN | 1559363 A | 1/2005 |

(Continued)

OTHER PUBLICATIONS

PCT International Search Report dated Nov. 3, 2014, Application No. PCT/US2014/043722, 2 pages.

(Continued)

*Primary Examiner* — Peter M. Cuomo
*Assistant Examiner* — Ifeolu A Adeboyejo
(74) *Attorney, Agent, or Firm* — Clark & Elbing LLP

(57) ABSTRACT

A head positioning aid includes at least one head positioning assistor and at least one securing member. Some head positioning aids include positioning members secured to a headwear member. The positioning members maintain an infant's head in midline. An optional cheek flap protects the skin on the face. An optional support member supports the neck and an open airway. Size adjustment members may also be used to secure and orient tubing for a nasal cannula.

11 Claims, 9 Drawing Sheets

(56) References Cited

U.S. PATENT DOCUMENTS

| | | | | |
|---|---|---|---|---|
| 1,713,049 A * | 5/1929 | Millson | ............... | A42B 1/12 |
| | | | | 2/200.3 |
| 2,106,570 A * | 1/1938 | Lipton | ............... | A42B 1/22 |
| | | | | 2/171.7 |
| 2,156,251 A * | 4/1939 | Carlson | ............... | A42B 1/22 |
| | | | | 2/175.1 |
| 4,631,766 A | 12/1986 | Semmler et al. | | |
| 4,864,662 A * | 9/1989 | Frank | ............... | A42B 1/22 |
| | | | | 2/183 |
| 5,075,903 A * | 12/1991 | Richoux | ............... | A42B 3/00 |
| | | | | 2/411 |
| 5,490,528 A * | 2/1996 | Day | ............... | A42B 1/04 |
| | | | | 132/200 |
| 5,799,335 A * | 9/1998 | Ethier | ............... | A42B 1/006 |
| | | | | 150/100 |
| 6,052,850 A | 4/2000 | Salido et al. | | |
| 6,238,413 B1 * | 5/2001 | Wexler | ............... | A61F 5/30 |
| | | | | 601/132 |
| 6,312,453 B1 | 11/2001 | Stefanile et al. | | |
| 6,321,403 B1 | 11/2001 | Matthews | | |
| 6,381,760 B1 * | 5/2002 | Lampe | ............... | A42B 3/00 |
| | | | | 2/414 |
| 6,397,399 B1 * | 6/2002 | Lampe | ............... | A42B 1/008 |
| | | | | 2/171.2 |
| 6,427,253 B1 * | 8/2002 | Penny | ............... | A42B 3/00 |
| | | | | 2/412 |
| 6,428,494 B1 * | 8/2002 | Schwenn | ............... | A61F 5/05891 |
| | | | | 2/414 |
| 6,481,020 B1 * | 11/2002 | Kirkland | ............... | A42B 1/041 |
| | | | | 2/171 |
| 6,536,058 B1 | 3/2003 | Chang | | |
| 6,647,553 B2 * | 11/2003 | Hoyez | ............... | A42C 5/04 |
| | | | | 2/195.1 |
| 6,718,557 B2 * | 4/2004 | Claro | ............... | A42B 1/22 |
| | | | | 2/195.2 |
| 6,758,526 B2 * | 7/2004 | Marbutt | ............... | B60N 2/2839 |
| | | | | 297/392 |
| 6,773,449 B2 * | 8/2004 | Wexler | ............... | A61F 13/12 |
| | | | | 606/204.15 |
| 6,857,150 B2 | 2/2005 | Matthews Brown et al. | | |
| 6,889,689 B1 | 5/2005 | Neuman | | |
| 6,939,316 B2 * | 9/2005 | Sklar | ............... | A61F 5/05891 |
| | | | | 128/857 |
| 6,954,954 B2 * | 10/2005 | Stelnicki | ............... | A47D 13/08 |
| | | | | 5/655 |
| 7,036,156 B2 * | 5/2006 | Lahman | ............... | A42B 1/08 |
| | | | | 2/181 |
| 7,614,098 B1 | 11/2009 | Quarry | | |
| 7,698,763 B2 | 4/2010 | Warnock | | |
| 7,761,933 B2 * | 7/2010 | Pham | ............... | A42C 1/00 |
| | | | | 2/410 |
| 8,096,304 B2 | 1/2012 | Scott et al. | | |
| 8,186,354 B2 | 5/2012 | Rogers et al. | | |
| 9,173,763 B2 * | 11/2015 | Gilmer | ............... | A61F 5/05883 |
| 2002/0007195 A1 | 1/2002 | Wexler | | |
| 2004/0181878 A1 | 9/2004 | Stelnicki | | |
| 2005/0193477 A1 * | 9/2005 | Penny | ............... | A63B 71/10 |
| | | | | 2/411 |
| 2006/0042013 A1 | 3/2006 | Madsen | | |
| 2007/0186931 A1 | 8/2007 | Zollinger et al. | | |
| 2007/0256242 A1 | 11/2007 | Warnock | | |
| 2007/0283502 A1 | 12/2007 | Tullous | | |
| 2008/0060134 A1 | 3/2008 | Virga | | |
| 2008/0184457 A1 | 8/2008 | Pham | | |
| 2010/0180381 A1 | 7/2010 | Verde Sanchez et al. | | |
| 2010/0257653 A1 | 10/2010 | Pitts | | |
| 2010/0281600 A1 | 11/2010 | Tagg | | |
| 2011/0091062 A1 | 4/2011 | Wittmann-Price et al. | | |
| 2011/0132379 A1 | 6/2011 | Lee | | |
| 2013/0146723 A1 | 6/2013 | Johnson et al. | | |
| 2013/0306081 A1 | 11/2013 | Devapatla et al. | | |

FOREIGN PATENT DOCUMENTS

| | | |
|---|---|---|
| CN | 201052196 Y | 4/2008 |
| CN | 201618216 U | 11/2010 |
| DE | 102004029034 B3 | 5/2005 |
| JP | 2010124848 A | 6/2010 |
| WO | 2000003666 A1 | 1/2000 |

OTHER PUBLICATIONS

Luther, "Positioning Devices", Poster displayed at the NICU Conference, Tampa FL, Jan. 2000.

Unknown, "Head Support Device for Infants", [online], CinisPREEMIERhalo [retrieved on Feb. 21, 2014]. Retrieved from the Internet: <URL: www.cinispremiehalo.com/design.html>.

Unknown, "Tortle Head Repositioning Systems for Micro=Preemies, Preemies, and Well Babies from 0-6 months", [online] Tortle mid-liner, [retrieved on Feb. 21, 2014]. Retrieved from the Internet <URL:http://tortlemidliner.com/our-products/>.

"Supportive Positioning Guideline." Wales Neonatal Network Guideline. www.walesneonatalnetwork.wales.nhs.uk/documentmap pp. 1-12. Dated Mar. 3, 2014. Accessed Nov. 29, 2016.

First Office Action dated Nov. 2, 2016 in connection with Chinese Patent Application No. 2014800462865, 16 pages, with English translation.

Examination report dated Feb. 6, 2017 in connection with Canadian Patent Application No. 2,916,471, 4 pages.

The extended European Search Report dated Jan. 2, 2017 in connection with European Patent Application No. 14813596.5, 7 pages.

Examination Report No. 1 dated Jan. 16, 2017 in connection with Australian Patent Application No. 2014284149, 8 pages.

First Examination Report dated Mar. 17, 2016 in connection with New Zealand Patent Application No. 715702, 3 pages.

Office Action for Japanese Patent Application No. 2016-521892, dated May 29, 2018 (12 pages).

* cited by examiner

HEAD POSITIONING AIDS FOR PREMATURE INFANTS

CROSS REFERENCE TO RELATED APPLICATIONS

The present application claims priority to U.S. Provisional Patent Application No. 61/838,050 filed 21 Jun. 2013 entitled "Head positioning aid for premature infants," and to U.S. Provisional Patent Application No. 61/930,898 filed 23 Jan. 2014, entitled "Head Positioning Aids for premature Infants," and each is hereby incorporated herein by reference in its entirety.

TECHNICAL FIELD

The technology described herein relates to head positioning aids and methods of using the same.

BACKGROUND

Prematurely born infants often suffer from, or are at risk of developing, numerous medical complications. For example, prematurely born infants are often at risk for intraventricular hemorrhage (IVH), which is bleeding into the fluid-filled ventricles of the brain due to fragile or immature cranial blood vessels. An estimated forty percent of prematurely born infants suffer from IVH. IVH can cause increased cranial and/or blood pressure, as well as disrupted flow of cerebrospinal fluid and hydrocephalus. IVH can also be fatal; it is the second leading cause of premature infant mortality. Long-term effects of IVH may include cognitive and developmental delays, cerebral palsy, and scoliosis.

Prematurely born infants are also often at risk for compromised cerebral blood flow and respiratory distress, and are often unable to maintain their body temperatures without assistance.

Prematurely born infants often require medical intervention to manage the aforementioned risks and to promote their health and viability. Common interventions include spinal taps, head shunts, nasal cannulas, nasal continuous positive airway pressure (CPAP), ventilator support, feeding tubes, and intravenous (IV) fluid support (such as via scalp IVs).

The standard of care includes midline supine positioning with a 30° incline for an initial 72-96 hours, which helps to reduce the risk of intraventricular hemorrhaging, as well as to promote optimal cerebral blood flow and uniform distribution of respiratory support to the lungs. This care is usually provided by rolling up soft materials, such as towels, and placing them around the infant's head to prevent it from moving. These materials are not secured to either the infant or to the surface on which the infant is placed (such as an incubator mattress), so they are easily disrupted and must be regularly repositioned to help maintain the infant in midline. These materials usually must be removed during examination of the infant, such as when taking X-rays, and later replaced. When a prematurely born infant is physiologically more stable, such as after the initial 72 to 96-hour midline supine positioning period, the infant may benefit from being positioned on the right and left side of the body. The head is maintained in midline, which helps to promote optimal cerebral blood flow.

Prematurely born infants have weak neck muscles and therefore limited ability to maintain the required positioning. They also have soft skulls and are at risk for developing dolichocephaly, a condition in which the head is disproportionately long and narrow, and which can result from external deformation related to head positioning.

Infants have delicate, sensitive skin that can easily be irritated or damaged. Medical tape placed on an infant's face or scalp, such as to secure nasal cannulas, feeding tubes, or scalp IVs, can be damaging to the skin.

The information included in this Background section of the specification, including any references cited herein and any description or discussion thereof, is included for technical reference purposes only and is not to be regarded as subject matter by which the scope of the invention as defined in the claims is to be bound.

SUMMARY

The technology disclosed herein relates to head positioning aids. The head positioning aids may be used to assist midline positioning of prematurely born infants, treat or prevent intraventricular hemorrhage, promote optimal cerebral blood flow, promote uniform distribution of respiratory support to the lungs, and treat or prevent dolichocephaly. While the discussion herein is focused on the effectiveness of the head positioning aids when used with premature infants, it should be understood that the head positioning aids may also be used with infants of full term gestation that have medical issues that require, or would be aided by, midline positioning.

In some embodiments, the head positioning aid comprises at least one head positioning assistor and at least one securing member. The head positioning assistor positions an infant's head in midline, and the securing member secures the infant's head to the positioning member, thereby maintaining the infant's head in the midline position.

In some embodiments, a neck support member is provided with the head positioning aid. The neck support member supports an infant's neck and promotes an open airway.

In one implementation, a method for using the head positioning aid, such as to support an infant's head in a midline position, is provided. The head of an infant and a head positioning assistor are placed adjacent to each other to position the infant's head in a midline position. A securing member is engaged to secure the infant's head to the positioning member, thereby maintaining the infant's head in the midline position.

In another implementation, a method for using the head positioning aid to help avoid or prevent intraventricular hemorrhage (IVH) is provided. The head of an infant and a head positioning assistor are placed adjacent to each other to position the infant's head in a midline position. A securing member is engaged to secure the infant's head to the positioning member, thereby maintaining the infant's head in the midline position, and the head is maintained in midline for a recommended therapeutic period (e.g., 72 hours). The head positioning aid may also be used in the treatment of IVH in the avoidance of further complications.

In some embodiments, the head positioning aid comprises positioning members secured to a headwear member. The headwear member is adjustable and secures the head positioning aid to the head of an infant. A front opening in the headwear member permits convenient placement and removal of the headwear member. The front opening also permits placement, removal, and monitoring of scalp IVs, and guides IV tubes away from the infant's face. The headwear member also secures nasal cannula or feeding tubes without medical tape. The positioning members minimize movement of an infant's head, maintain an infant's head in midline, and deflect an infant's moving head back to midline. The headwear may also be breathable and allow heat to dissipate from the infant's head to avoid overheating.

In some embodiments, cheek flaps are provided with the headwear and positioning aids. The cheek flaps protect the skin of an infant's face from damage caused by nasal cannulas or feeding tubes.

In some embodiments, a support member is provided with the headwear and positioning aids. The support member supports an infant's neck and promotes an open airway.

In one implementation, a method for using the head positioning aid, such as to support an infant in a midline position, is provided. The headwear member is applied over the infant's head and the front opening is guided over or around scalp IVs or other medical devices (e.g., monitoring devices and wires) connected to the infant's head, which minimizes stress on the infant. When the front opening is closed, the scalp IV tubes are directed and secured away from the infant's face. The size of the headwear member is adjusted to fit the head of the infant and is secured at its adjusted size, which also secures a nasal cannula or feeding tube without the use of medical tape on an infant's face or elsewhere. The positioning members are positioned on either side of the infant's head and help to prevent the head from moving. The infant's head is thereby maintained in a midline position with respect to the spine of the infant when the infant is supine.

In another implementation, a method for using the head positioning aid, such as to support an infant's head in midline and to treat or prevent dolichocephaly while the infant is lying on its side, is provided. The headwear member is applied and adjusted as described above. The front opening is positioned between the center of the forehead and the ear on which the head is not resting. The positioning members are positioned towards the front and back of the infant's head and help to prevent the head from moving. The infant's head is thereby maintained in a midline position with respect to the spine of the infant when the infant is lying on its side. Further, the positioning members provide a rounding effect on the sides of the head (and the back of the head when in a midline position) to counter possible dolichocephaly if the head were to be merely placed on a flat surface.

In another method for using the head positioning aid, the infant's head rests on, but is not covered by, the headwear member. The positioning members maintain the infant's head in midline as described immediately above.

In another implementation, a method for using the head positioning aid including a cheek flap, such as to protect the skin of an infant's face, is provided. The headwear member and positioning members are used according to any method described above. The cheek flap is positioned between an infant's face and a nasal cannula or feeding tube, which helps to protect the skin of an infant's face from damage by the nasal cannula feeding tube.

In another implementation, a method for using the head positioning aid including a support member, such as to support the neck of an infant and promote an open airway, is provided. The headwear member and positioning members are used according to any method described above. The support member, which may be secured to the headwear member, is positioned under the neck of an infant. The infant's neck is thereby supported in a position that promotes an open airway, which may be helpful for any prematurely born infant, including one who requires respiratory support.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

DETAILED DESCRIPTION

Figure 1A:
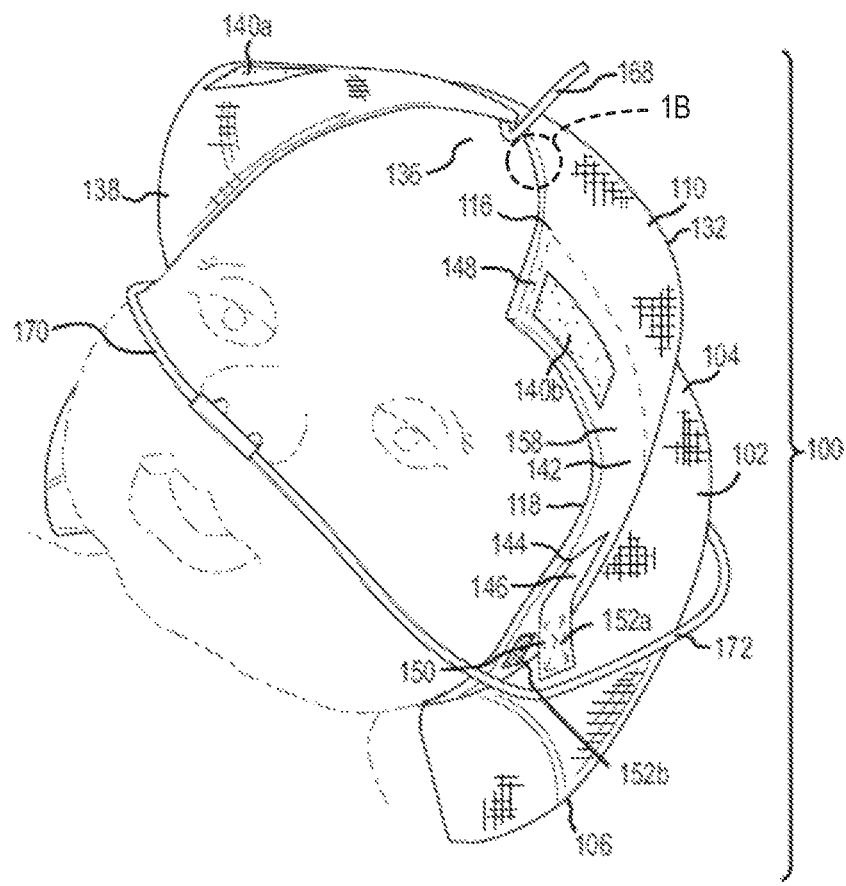
FIG. 1 is a front right isometric view of a head positioning aid according to one embodiment applied to an infant's head.

Head positioning aids primarily for use with the treatment of premature infants are disclosed herein. The head positioning aids may be generally understood as having at least one head positioning assistor and at least one securing member. The head positioning assistor is capable of positioning an infant's head in midline. The securing member secures the infant's head to the positioning member, thereby maintaining the infant's head in the midline position for a recommended therapeutic period.

The head positioning assistor may be any element that is capable of positioning an infant's head in midline. Exemplary head positioning members include, but are not limited to, pillows comprising a solid upper surface; pillows comprising a depression or cut-out for the head; seats, basins, molds, pads, or mattresses for supporting or positioning the body of an infant that extend towards and adjacent to or around the head; bedding; towels; rolls comprising a resilient and/or compression-resistant material, such as solid foam, memory foam, stuffing, batting, down, synthetic down-like material, gel, or a combination thereof; lateral supports; circumferential supports; and material connecting lateral or circumferential supports.

The securing member may be any element that maintains the head of an infant in a midline position when the securing member is engaged. Exemplary securing members include, but are not limited to, headbands; webbing for the head; caps; clothing comprising one or more components that extend towards and adjacent to or over the head; straps; ties;

buckles; headbands; and fasteners, which may include, for example, buttons, snaps, hook-and-loop fasteners (e.g., Velcro), or hook-and-eye fasteners.

The securing member may be engaged by any means known in the art. For example, a pad may be positioned with respect to an infant's head by securing it to a headband, webbing for the head, or a cap. As another example, a tie securing member may be engaged by tying it such that it lies across the forehead or other part of an infant's head. As a further example, a buckle securing member may be engaged by buckling it such that it lies across the forehead or other part of an infant's head. As a still further example, a fastener securing member may be engaged by releasably attaching opposing components of a fastener, such as inserting a button in a buttonhole or pressing hooks and loops of Velcro together.

In some embodiments, the securing member is permanently or releasably attached to the head positioning assistor. For example, a buckle securing member may be permanently attached to a pillow head positioning assistor, such as by glue or sewn threads. As another example, a strap securing member may be releasably attached to a clothing head positioning assistor by threading it through loops on the clothing. As another example, a pad may be releasably attached to a headband securing member by placing the pad in a pocket on the headband securing member. As a further example, and as depicted in FIGS. 1-4 (described in more detail below), lateral support securing members are sewn onto a cap head positioning assistor.

In some embodiments, the securing member is permanently or releasably attached to the surface on which the infant is resting, which surface may or may not also be a head positioning assistor. For example, a tie securing member may be attached to a seat, basin, mold, pad, or mattress on which an infant is resting. The tie securing member may be engaged over an infant's head without being attached to or contacting a head positioning assistor. As another example, a Velcro securing member may be attached to a mattress on which an infant is resting. The Velcro securing member may be engaged by releasably attaching to Velcro on a cap head positioning assistor.

In the construction and use of the head positioning assistors and securing members, their size, shape, material, and attachment to or separation from each other may help avoid or prevent intraventricular hemorrhage, promote optimal cerebral blood flow by ensuring carotid arterial and jugular venous blood flow, promote uniform distribution of respiratory support to the lungs, and treat or prevent dolichocephaly.

In some implementations, the head positioning aids include a neck support member. A neck support member may be any element that is capable of supporting the neck of an infant. A neck support member may also promote an open airway. Exemplary neck support members include, but are not limited to, rolls comprising a compression-resistant material, such as foam; pillows; clothing comprising a component that extends towards and behind the neck; bedding; and towels.

A neck support member may be physically separate from but used in conjunction with the head positioning aids. Alternatively, a neck support member may be permanently or releasably secured to the head positioning aid. For example, a roll neck support member may be secured to a cap by stitches, glue, tape, bonding, fasteners, or any combination thereof. As another example, a pillow neck support member may be secured to a mattress by engaging opposing Velcro pieces on the pillow and mattress.

Methods of Use of the Head Positioning Aid

By way of example, but not limitation, the head positioning aids described above may be used to support an infant in a midline position according to the following procedure. A head positioning assistor is placed on or adjacent to the head of an infant. As an example, at least the head of an infant is placed on a pillow, seat, basin, mold, pad, or mattress head positioning assistor such that the infant rests in a supine position or on its side. As a further example, bedding, towels, rolls, lateral support, or circumferential support head positioning assistors are placed adjacent to the infant's head while the infant is in the supine position or is lying on its side. As a still further example, the infant's head is placed on material connecting lateral or circumferential supports such that the infant rests in a supine position or on its side, or the material is slid behind the infant's head while the infant is in the supine position or is lying on its side.

A securing member is then engaged with respect to the head positioning assistor and the infant's head to maintain the infant's head in a midline position with respect to the spine, whether the infant is supine or lying on its side. For example, a pad head positioning assistor may be engaged by securing it to a headband, webbing for the head, or cap. As another example, a tie securing member connected with a head positioning assistor is engaged by tying it such that it lies across the forehead or other part of the infant's head. As a further example, a buckle securing member connected with a head positioning assistor is engaged by buckling it such that it lies across the forehead or other part of the infant's head. As a still further example, a fastener securing member connected with a head positioning assistor is engaged by inserting a button in a buttonhole or pressing hooks and loops of Velcro together.

In another embodiment, the head positioning assistor and the securing member may be components of single, unitary head positioning aid. A securing member is placed on or adjacent to the head of an infant with the head positioning assistor attached thereto. For example, a cap, webbing for the head, a headband, or other headwear may have a pair of lateral support members attached thereto. The headware is guided onto the infant's head while the infant is in the supine position or is lying on its side and positioned on the head such that the lateral support securing member is adjacent to the infant's head and positioned to hold the infant's head in a midline position with respect to the spine, whether the infant is supine or lying on its side.

The head positioning aids described above may be used to avoid or prevent intraventricular hemorrhage in an infant according to the following procedure. The head of an infant and a head positioning assistor are placed adjacent to each other according to any of the examples described above. A securing member is engaged to maintain the infant's head in a midline position with respect to the spine according to any of the examples described above.

The infant's head may be maintained in a midline position for a desired therapeutic period. In some instances, such a period can be as long as 72-96 hours. Temporarily and as often as necessary, the infant's head may be moved from the midline position, the securing member may be disengaged, and/or the head positioning assistor may be moved away from the head, all in order to provide care for the infant, such as to determine the status of the infant, provide medical assistance, or change a diaper.

A neck support member may be used in conjunction with any of the methods described above. By way of example, but not limitation, a head positioning aid may be used with a support member to support an infant's head in a midline position or to avoid or prevent intraventricular hemorrhage, as well as to support the neck of an infant and promote an open airway, according to the following procedure. The infant's head and a head positioning assistor are placed adjacent to each other according to any of the procedures described above. The neck support member may already be attached to the head positioning assistor, it may be slid behind the neck of an infant after the head positioning assistor has been positioned, or the infant may be placed such that its neck rests on the neck support member. The neck support member helps support an infant's head or neck. The support member also helps promote an open airway and uniform distribution of respiratory support to the lungs, such as when an infant is on a ventilator.

A securing member is engaged to maintain the infant's head in a midline position with respect to the spine according to any of the procedures described above. The securing member may be engaged before or after the neck support member has been positioned.

Head Positioning Aid Comprising Two Positioning Members

In some implementations, the head positioning aids may be generally understood as having positioning members (i.e., a head positioning assistor) secured to a headwear member (i.e., a securing member). The positioning members maintain an infant's head in midline. In some implementations, a front opening in the headwear member assists in applying the headwear member to an infant's head with minimal stress on the infant, and provides access to the scalp for placement, removal, or monitoring of scalp IVs. In some implementations, the headwear member is adjustable. In some embodiments, nasal cannula or feeding tubes may be secured to the headwear member without the use of medical tape on an infant's face or elsewhere.

FIGS. 1-4 depict one embodiment of a head positioning aid 100. The head positioning aid 100 comprises positioning members 102 secured to a headwear member 110, which comprises a front opening 136 and an adjustment member 146. While two positioning members 102 are shown in the figures as separate members spaced laterally apart from each other, a single U-shaped or V-shaped positioning member could also be used so long as two lateral support members are provided as part of the single positioning member along lateral sides of the head to prevent side-to-side movement or rolling thereof.

The positioning members 102 may be comprised of a filler. The filler may be, for example, solid foam, memory foam, stuffing, batting, down, synthetic down-like material, gel, or a combination thereof. The filler may be resilient such that it returns to its original shape, or close to its original shape, after being compressed. The filler may be of sufficient quantity, compactness, or firmness that it resists complete compression by the weight of an infant's head. The filler may be partially compressible, but has enough compression resistance that it helps each positioning member 102 minimize movement of an infant's head, maintain an infant's head in midline, and deflect an infant's moving head back to midline. The compression resistance may be matched to the size and weight of an infant's head, or to the force exerted by an infant's moving head. For example, the filler may compress to about fifty percent or less of its uncompressed thickness when weighted under an infant's head.

Each positioning member 102 may include a casing, such as a fabric casing. The casing may completely or partially surround the filler. The casing may be constructed with one more seams 130.

Figure 3:
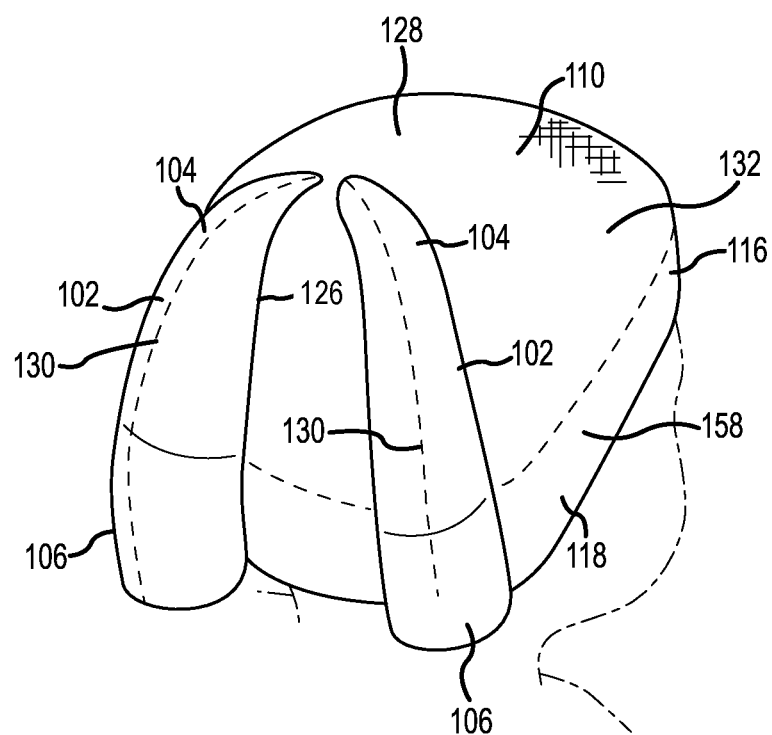
FIG. 3 is a left rear isometric view of the head positioning aid of FIG. 1 applied to an infant's head.
Figure 4:
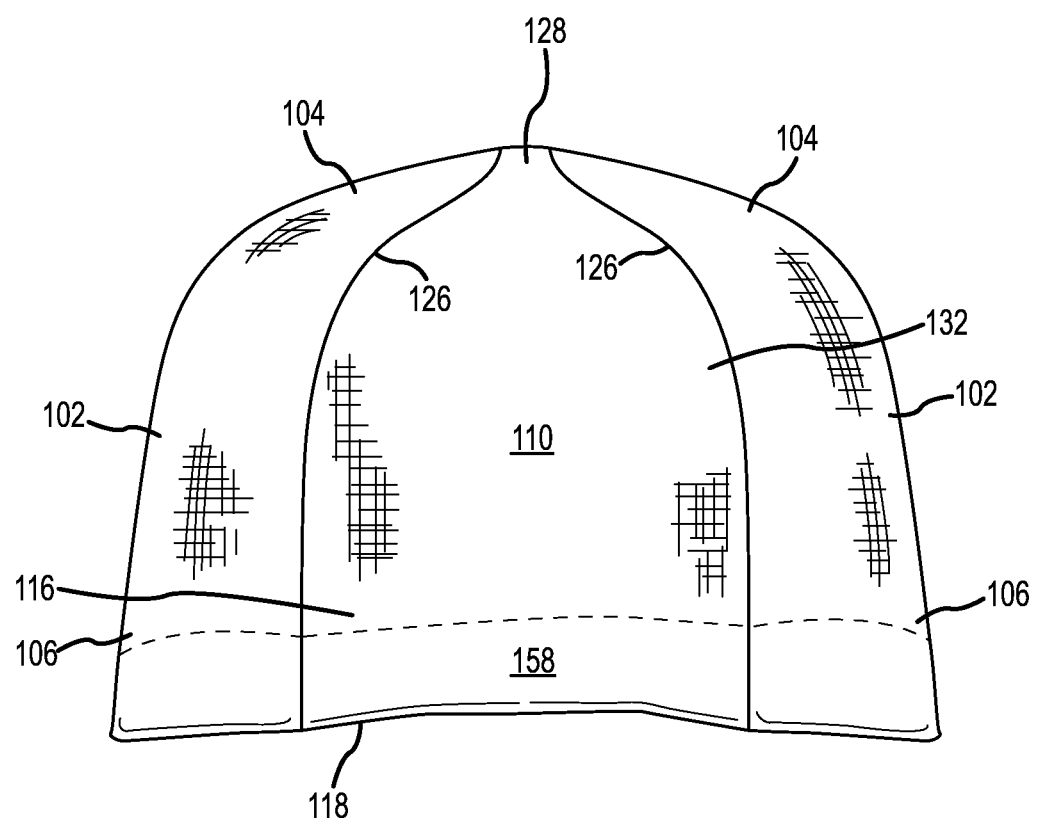
FIG. 4 is a rear elevation view of the head positioning aid of FIG. 1.

With reference to FIGS. 3 and 4, each positioning member 102 may be substantially arc- or crescent-shaped. For example, each positioning member 102 may generally follow the curvature of the top, back, and/or sides of an infant's skull. The positioning members 102 may each have the same or be of different sizes, and may each have the same shape or have different shapes. Each positioning member 102 has an upper end 104 positioned at or near the apex 128 of the headwear member 110, and has a lower end 106 positioned at or near the lower portion 116 of the headwear member 110. Each positioning member 102 may be the same length as, shorter than, or longer than, the length of the headwear member 110 at the location to which that positioning member 102 is secured. Thus, the upper end 104 may extend beyond the apex 128 of the headwear member 110, extend to the apex 128 of the headwear member 110, or terminate below the apex 128 of the headwear member 110. The lower end 106 may extend beyond the lower portion 116 of the headwear member 110, extend to the lower portion 116 of the headwear member 110, or terminate above the lower portion 116 of the headwear member 110.

Each positioning member 102 is elongated such that its length is greater than either its width or depth (thickness). The length of a positioning member 102 may be 2 to 6 times greater than its thickness at the lower end 106. For example, the length of a positioning member 102 may be about 4 times greater than its thickness at the lower end 106. The longitudinal elongation may help a positioning member 106 maintain an infant's head in midline and deflect an infant's moving head back to midline.

Each positioning member 102 extends outward from the outer surface of the headwear member 110. Each positioning member 102 may extend away from the headwear member 110 for the same distance along the entire length of the positioning member 102, or the extension distance (thickness) may vary along the length of the positioning member 102. Each positioning member 102 may be thicker at its lower end 106 than at its upper end 104. For example, a positioning member 102 may have nominal thickness at the upper end 104 and a functional thickness at its lower end 106. The thickness at the lower end 106 may be enough to help the positioning member 102 maintain an infant's head in midline and deflect an infant's moving head back to midline. In one embodiment, the lower end 106 is 1 to 3 inches thick.

With reference to FIGS. 3 and 4, a positioning member 102 may have the same lateral distance (width or diameter) along the entire length of the positioning member 102, or the width may vary along the length of the positioning member 102. A positioning member 102 may be wider or have a larger diameter at its lower end 106 than at its upper end 104. The lower end 106 may be 1.25 to 3 times as wide as the upper end 104. For example, the lower end 106 may be about twice as wide as the upper end 104. In one embodiment, the lower end 106 is 0.5 to 2 inches wide. In another embodiment, the lower end 106 is about 1 inch wide.

The thickness of the lower end 106 of a positioning member 102 may be greater than, less than, or equal to, its width. In one embodiment, the thickness of the lower end 106 of a positioning member 102 is 1.25 to 3 times the width of the lower end 106 of that positioning member 102. In another embodiment, the thickness of the lower end 106 of a positioning member 102 is about twice the width of the lower end 106 of that positioning member 102. In another embodiment, the thickness of the lower end 106 of a positioning member 102 is about 2 inches and the width of the lower end 106 of that positioning member 102 is about 1 inch.

Each positioning member 102 is secured to a headwear member 110. In one embodiment, as shown in FIGS. 1-4, the headwear member 110 is a cap. The cap may be any cap known in the art including, but not limited to, a skullcap or a beanie cap. The overall shape of the headwear member 110 approximates at least a portion of an infant's skull. The headwear member 110 may fit closely or snugly over at least a portion of an infant's skull.

The headwear member 110 of the exemplary embodiment has an apex 128, a dome portion 132, a lower portion 116, and a front opening 136. The apex 128 may include one or more closures of one or more pieces of fabric. A closure may be by any means known in the art including, but not limited to, stitches, glue, tape, bonding, fasteners, or any combination thereof. Fasteners may include, for example, buttons, snaps, hook-and-loop fasteners (e.g. Velcro), or hook-and-eye fasteners. The closure may be formed with one or more seams.

The dome portion 132 extends from the apex 128 to the lower portion 116 of the headwear member 110. When the head positioning aid 100 is worn by an infant, the dome portion 132 covers the infant's head from the crown to approximately the location of the infant's ears.

Figure 1B:
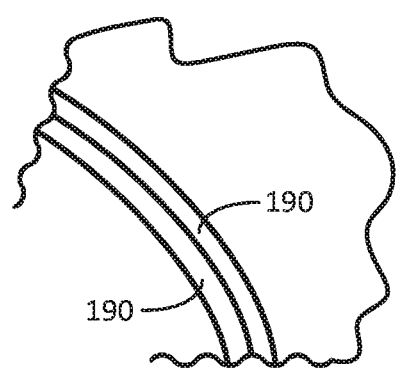
Figure 6:
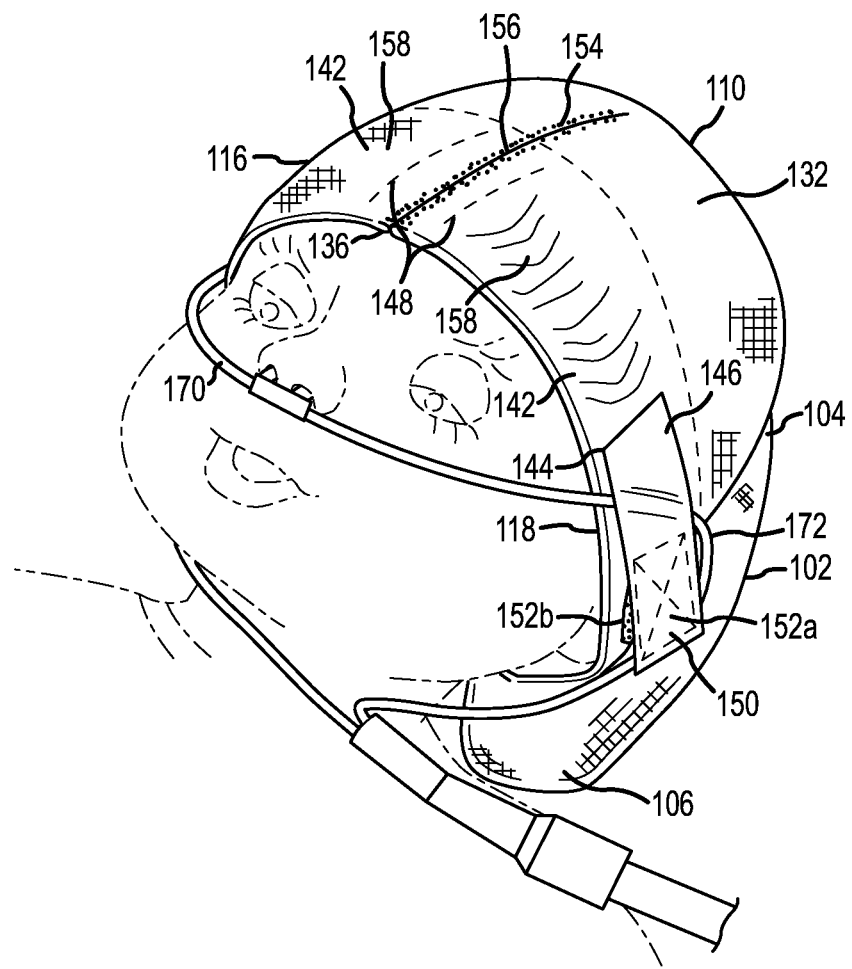
FIG. 6 is a front right isometric view of a head positioning aid according to another embodiment applied to an infant's head.
Figure 8:
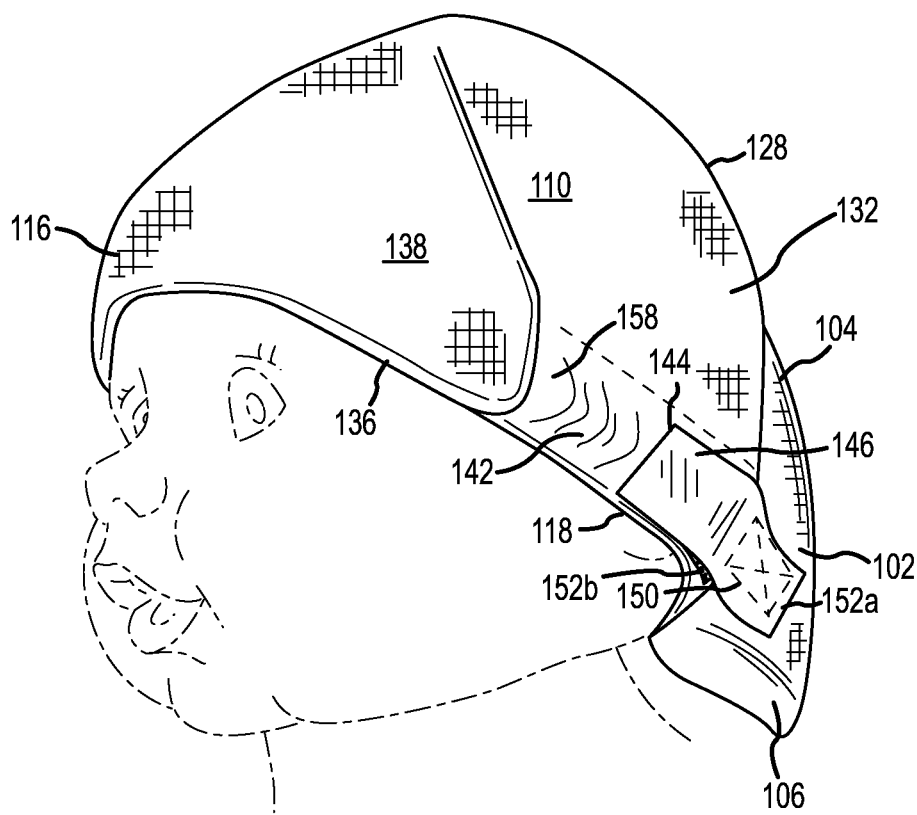
FIG. 8 is a front right isometric view of the head positioning aid of FIG. 1 applied to an infant's head.

The front opening 136 is positioned between positioning members 102 on the front side of the headwear member 110. For example, as shown in FIGS. 1, 6, and 8, the front opening 136 may be positioned approximately in the center of the front side of the headwear member 110. The front opening 136 extends from the bottom edge of the lower portion 116 of the headwear member 110 toward the apex 128. The front opening 136 may terminate in the dome portion 132 or at or near the apex 128.

The front opening 136 is releasably closable. When in the open position, the front opening 136 helps to minimize disturbance to and stress on an infant while the head positioning aid 100 is being put on and taken off an infant. For example, the front opening 136 can be guided over or around scalp IVs 168 so as to not disturb them or the infant. When the head positioning aid 100 is being worn by an infant and the front opening 136 is in the open position, a portion of the infant's skull is exposed, which allows for placement, removal, and monitoring of scalp IVs 168. The front opening 136 can be partially or completely opened or closed for temperature monitoring, regulation, and stabilization.

Access to the infant's skull is maintained when the front opening 136 is in the closed position. For example, tubes, such as from scalp IVs 168, can pass through or under the front opening 136. The tubes can be positioned directed toward a desired location, such as away from the infant's face.

Figure 2:
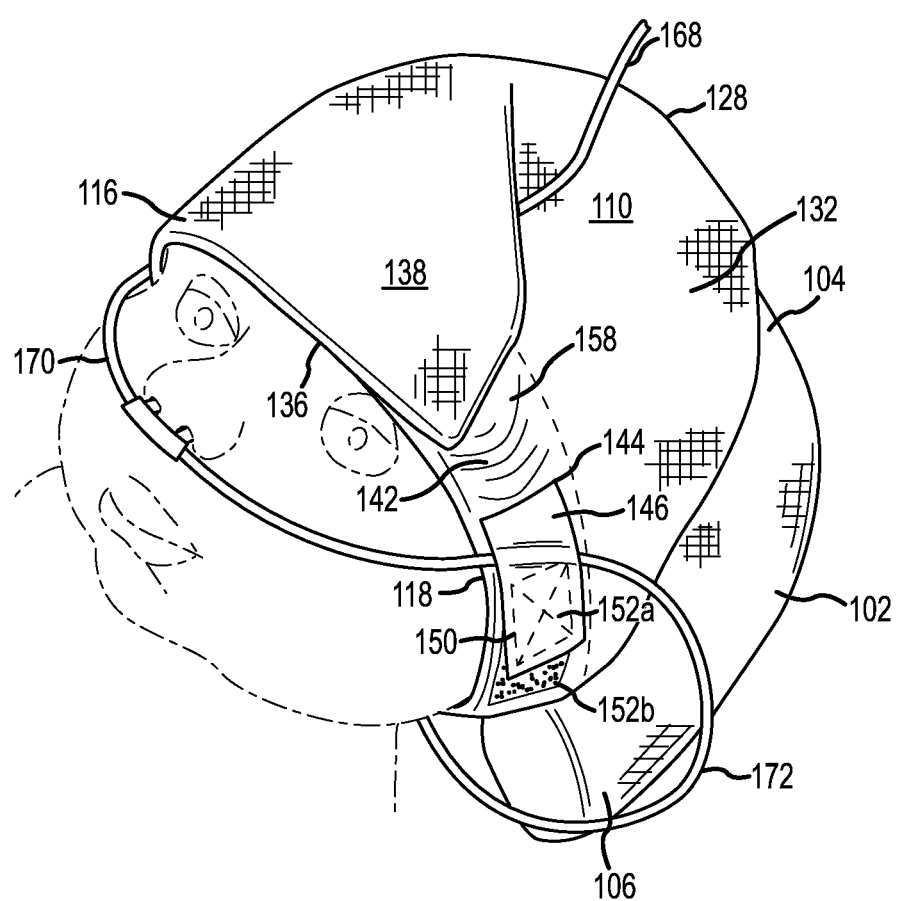
FIG. 2 is a front right isometric view of the head positioning aid of FIG. 1 applied to an infant's head with the flap in the closed position.

In one embodiment, as shown in FIGS. 1 and 2, the front opening 136 comprises a flap 138. The flap 138 may be any size and shape, such as substantially triangular in shape. When the front opening 136 is in the open position (see FIG. 1), the flap 138 may be folded back such that it lays on top of a portion of the headwear member 110.

When the front opening 136 is in the closed position (see FIG. 2), the flap 138 lays substantially flat on the infant's skull. The flap 138 can be secured to the headwear member 110 at one or more flap attachments 140a, 140b. The flap attachments 140a, 140b may include, for example, buttons, snaps, hook-and-loop fasteners, or hook-and-eye fasteners. In the exemplary embodiment of FIG. 1, the flap attachments 140a, 140b are hook-and-loop fasteners. One flap attachment 140a is positioned on the underside of the flap 138 and another flap attachment 140b is positioned on the lower portion 116 of the headwear member 110.

In another embodiment, as shown in FIG. 6, the front opening 136 comprises a slit 154. When the front opening 136 is in the open position (not shown), the portion of the headwear member 110 on either side of the slit 154 may be folded back such that it lays on top of another portion of the headwear member 110.

When the front opening 136 is in the closed position (see FIG. 6), the front of the headwear member 110 lays substantially on the infant's skull. In the closed position, the sides of the slit 154 may meet or may overlap. The front opening 136 can be secured in the closed position at one or more fasteners 156. The fasteners 156 may include, for example, buttons, snaps, hook-and-loop fasteners, or hook-and-eye fasteners. In one embodiment, the slit 154 may be fastened only at its bottom edge such that a length of the slit 154 remains substantially open, for example, to allow for exit of a cranial IV tube.

The circumference of the lower portion 116 defines a lower opening 118. When the front opening 136 is in the closed position, the lower opening 118 may be substantially circular or oval in shape.

The lower portion 116 of the headwear member 110 may terminate in an edge that may be smooth or rounded so as to be comfortable against an infant's head. When worn by an infant, the lower portion 116 may lie near, on, or over the infant's ears.

The lower portion 116 may include a trim such as a band, a turn-up portion, piping, or binding. The trim may be any fixed or adjustable width. For example, a trim that is a turn-up portion may be folded up or down to a greater or lesser degree to adjust its height. The trim may be decorative or functional. For example, a turn-up portion may allow adjustment in how far down along an infant's head the headwear member 110 extends.

The lower portion 116 may include one or more hems 158. A hem 158 may extend partially or completely around the lower portion 116. A hem 158 may be any width. The width may be the same for the entire length of a hem 158, or the width may vary.

At least a portion of a hem 158 may form a pocket 142. In one embodiment, as shown in FIGS. 1, 2, 5B, and 6-8, a portion of a hem 158 on either side of the front opening 136 forms a pocket 142. Each pocket 142 is at least wide enough to accommodate an adjustment member 146.

A headwear member 110 may include one or more adjustment members 146. An adjustment member 146 may be or comprise a stretchable material, such as elastic, an elasticized fabric, or elasticized drawstrings. An adjustment member 146 has a fixed end 148 and a free end 150. The fixed end 148 is secured to the lower portion 116 of the headwear member 110. For example, the fixed end 148 may be secured to the inside of a pocket 142. The fixed end 148 may be secured to the lower portion 116 by any known means, such as by sewing. A portion of the fixed end 148 may extend beyond a pocket 142. Alternatively, a fixed end 148 may terminate inside a pocket 142. As shown in FIGS. 1 and 6, a fixed end 148 may terminate inside a pocket 142 and near or at the front opening 136.

The adjustment member 146 may pass through an opening 144 in the hem 158. The opening 144 may be positioned between the front opening 136 and a positioning member 102 on the same side of headwear member 110. The adjustment member 146 may pass through an opening 144 such that the fixed end 148 is inside the pocket 142 and the free end 150 is outside of the pocket 142. The opening 144 may be on the outer surface or inner surface of the headwear member 110.

In some implementations, the size of the headwear member 110 can be adjusted by pulling on or releasing the free end 150 of the adjustment member 146. Pulling on the free end 150 can tighten the fit of the headwear member 110, such as by decreasing the effective circumference of the lower portion 116. In the exemplary embodiments depicted in FIGS. 2, 5B, and 6-8, pulling on the free end 150 causes the fabric of the hem 158 that creates the pocket 142 to gather together, thereby decreasing the effective circumference of the lower portion 116. Releasing the free end 150 lets out the gathers in the fabric of the hem 150 that creates the pocket 142, thereby increasing the effective circumference of the lower portion 116. The adjustment member 146 helps fit the headwear member 110 to all sizes of infants' heads.

An adjustment member 146 may be releasably secured to the headwear member 110 at one or more adjustment member attachments 152*a*, 152*b*. An adjustment member attachment 152*a*, 152*b* may be any releasable attachment known in the art. Securing the adjustment member 146 helps maintain the adjusted size of the headwear member 110 until the adjustment member 146 is released.

An adjustment member attachment 152*a* may be in or on the adjustment member 146, such as at or near the free end 150. An adjustment member attachment 152*b* may be in or on the headwear member 110, such as in or on the hem 158 between an opening 144 and a positioning member 102 on the same side of the headwear member 110 as the opening 144.

Two adjustment member attachments 152*a*, 152*b* may operate as a functional pair. For example, as depicted in FIGS. 1, 2, 5B, and 6-8, the adjustment member attachments 152*a*, 152*b* may be Velcro. An adjustment member attachment 152*a* is on the underside of the free end 150 of each adjustment member 146. An adjustment member attachment 152*b* is also on the hem 158 of the headwear member 110 on each side (i.e. front left side and front right side) of the headwear member 110 about midway between the front opening 136 and a positioning member 102. The adjustment member 146 may be secured to the headwear member 110 by pressing the portion of the Velcro-adjustment member attachment 152*a* closest to the free end 150 to the Velcro-adjustment member attachment 152*b* of the headwear member 110. Securing the adjustment member 146 to the headwear member 110 at a portion of the Velcro-adjustment member attachment 152*a* closer to the fixed end 148 maintains a smaller effective size of the headwear member 110 than when the adjustment member 146 is secured to the headwear member 110 at the portion of the Velcro-adjustment member attachment 152*a* closest to the free end 150.

As another example, the adjustment member attachments in the adjustment member 146 may be a series of two or more button holes that run from the free end 150 toward the fixed end 148. An adjustment member attachment on the headwear member 110 may be a button. The adjustment member 146 may be secured to the headwear member 110 by buttoning the button-adjustment member attachment to the button hole-adjustment member attachment closest to the free end 150. Securing the adjustment member 146 to the headwear member 110 at a button hole-adjustment member attachment closer to the fixed end 148 maintains a smaller effective size of the headwear member 110 than when the adjustment member 146 is secured to the headwear member 110 at the button hole-adjustment member attachment closest to the free end 150.

A medical device, such as a feeding tube or nasal cannula 170, may be secured to the headwear member 110. For example, a nasal cannula tube 172 may be captured when an adjustment member 146 is attached to the headwear member 110 at an adjustment member attachment 152*a*, 152*b*. In the exemplary embodiment depicted in FIGS. 2, 6 and 7, a nasal cannula tube 172 is captured between the adjustment member 146 and the headwear member 110. The nasal cannula tube 172 is positioned between the free end 150 of the adjustment member 146 and the opening 144 in the hem 158. Securing a nasal cannula 170 or other device to the headwear member 110 helps to selectively position the device. Securing a nasal cannula 170 or other device to the headwear member 110 also helps to avoid placing medical tape on an infant's face, which is a known deficiency of the current standard of care as the tape can irritate or abrade the infant's skin upon removal.

The headwear member 110 may be constructed of any one or more soft fabric materials known in the art. The fabric material may be any natural or synthetic fabric such as cotton, elastane or spandex, microfiber, polyester, rayon, silk, viscose, or wool, or any combination thereof. The fabric may be woven, unwoven, or knit. A knit may be a smooth or ribbed knit. The material may be flexible, stretchable, wicking, breathable, cooling, fire retardant, machine washable, or any combination thereof.

In the construction and use of the headwear member 110, a material that is stretchable may help secure the headwear member 110 to an infant's head. A material that is stretchable may also provide versatile adjustability in both circumference of the headwear member 110 and height of the headwear member 110. A stretchable material may evenly apply an elastic-like grip around the circumference of the headwear member 110 for a comfortable fit that is also resistant to unintentional movement, such as rotating around an infant's head or slipping up or down on an infant's head.

Stretchable materials may include stretchable fabrics such as, for example, elastane or spandex, nylon, and ribbed knits. A ribbed knit may be highly stretchable across its series of ribs. If a ribbed knit is used in the construction of the headwear member 110 of FIGS. 1-4 such that the ribs are oriented approximately vertically (i.e., from the apex 128 to the lower portion 116 of the headwear member 110), the stretching ability is concentrated around the circumference of the headwear member 110. The fabric may stretch across the ribs by a factor of about two, about three, or about four. The fabric may stretch along the ribs to a lesser degree than across the ribs. For example, the fabric may stretch along the ribs by a factor of about one half to about one.

The stretch of a fabric may be limited by structures such as seams. The stretch of a fabric may also be limited by increasing the number of layers of fabric or overlaying a stretchable fabric and a non-stretchable fabric. Alternately, the fabric may be reinforced with elastic strips or bands that grip the infant's head.

In the construction and use of the headwear member 110, a non-insulating fabric may help prevent an infant's body temperature from rising or reduce an infant's body temperature as compared to an insulating fabric. Non-insulating fabrics include fabrics that are wicking, breathable, and/or cooling.

A wicking fabric draws moisture away from skin and may also transfer it to a next, more outer, layer. Drawing moisture, usually perspiration, away from the skin helps regulate body temperature. For example, drawing moisture away from the skin helps a person feel or stay warmer in cool or cold environments and helps a person feel or stay cooler in warm or hot environments. A wicking fabric may help an infant regulate body temperature. Wicking fabrics may include, for example, cotton, microfiber, polyester, silk, and wool. Wicking fabrics may also include performance-engineered synthetic fabrics such as Capilene® (Patagonia, Ventura, Calif.), FlashDry™ (The North Face, San Leandro, Calif.) and DriClime® (Marmot, Rohnert Park, Calif.).

A breathable fabric allows air to reach the skin and allows water vapor to escape from the fabric. Allowing air to reach the skin and allowing water vapor, usually from perspiration, to escape from the fabric helps to reduce body temperature and/or prevent body temperature from rising. A breathable fabric may help an infant stay cooler. Breathable fabrics may include, for example, cotton, linen, and silk. Breathable fabrics may also include performance-engineered synthetic fabrics such as Gore-Tex® (breathable and waterproof; W. L. Gore & Associates, Elkton, Md.), OmniTech® (breathable and waterproof; Colombia Sportswear Co., Portland, Oreg.) and PolarTec® (breathable and insulating; Marmot, Rohnert Park, Calif.).

A cooling fabric allows heat to pass away from the skin through the fabric and does not reflect heat back to the skin. Allowing heat to pass through the fabric helps to reduce body temperature and/or prevent body temperature from rising. A cooling fabric may help an infant stay cooler. Cooling fabrics may include, for example, cotton, linen, and rayon.

The headwear member 110 may be constructed of one or more layers of soft materials, such as one layer. Each layer may be constructed of one or more pieces joined together by any means known in the art including, but not limited to, stitches, glue, tape, bonding, or any combination thereof. The one or more pieces may meet at one or more seams.

The positioning member 102 is secured to the headwear member 110 within a covering fabric. The covering fabric may be the fabric of the headwear member 110 or may be a separate piece of fabric, such as a casing.

The positioning members 102 may be attached at lateral positions on a rear surface of the headwear member 110. In the exemplary embodiment depicted in FIG. 3, a positioning member 102 is positioned on each of the left and right sides of the headwear member 110, toward the back of the headwear member 110. The positioning members 102 meet or nearly meet at or near the apex 128. With reference to FIGS. 1-4, 5B, 6, and 7, the positioning members 102 are positioned behind the ears of an infant when the head positioning aid 100 is in use. With reference to FIG. 8, a positioning member 102 is positioned towards each of the front and back sides of the infant's head when the head positioning aid 100 is in use.

The positioning members 102 minimize movement of an infant's head, maintain an infant's head in midline, and deflect an infant's moving head back to midline. The positioning members 102 may be positioned laterally when an infant's head is in a midline position, which diminishes pressure to the side of the face and head and thereby helps to prevent the development of dolichocephaly. The positioning members 102 may be positioned toward the front and back of the head when an infant is lying on its side, which diminishes pressure to the side of the head between the positioning members 102 and thereby helps to prevent the development of dolichocephaly.

Each positioning member 102 is secured to the headwear member 110 at one or more junctures 126. A juncture 126 may be formed by any known means including, but not limited to, stitches, glue, tape, bonding, or any combination thereof. A juncture 126 may include a seam.

A juncture 126 may extend partially or completely along the length of the positioning member 102. A juncture 126 may extend to or near the apex 128 of the headwear member 110. A juncture 126 may extend to or near the lower portion 116 of the headwear member 110. A juncture 126 may extend partially or completely along the width of the positioning member 102 at any point along the length of the positioning member 102.

Multiple junctures 126 may meet or overlap. One juncture 126 may transition into another, adjacent juncture 126. For example, if two or more junctures 126 are created by sewing, stitches may continue unbroken from one juncture 126 to an adjacent juncture 126. As another example, four junctures 126, one on each of the left, right, top, and bottom sides of a positioning member 102, may be formed by one continuous string of stitches.

A juncture 126 may secure a portion of the headwear member 110 to a minor portion, such as an edge, thin strip, small piece, or casing, of a positioning member 102. A juncture 126 may secure one portion of the fabric of the headwear member 110 to another portion of the fabric of the headwear member 110 such that a positioning member 102 is captured by the fabric of the headwear member 110, as in pocket. The pocket may be nominally larger than the positioning member 102 such that the positioning member 102 has no or limited room to move within the pocket.

In one embodiment, two laterally separated longitudinal junctures 126 extending along the length of the positioning members 102 may be used to attach and support each positioning member 102. When a positioning member 102 is secured to the headwear member 110 by more than one lateral juncture 126, the lateral junctures 126 help the positioning member 102 resist lateral rolling, pivoting, and/or bending. The junctures 126 may provide a sturdier base of support on the headwear member 110 for the positioning member 102 than does a single juncture.

When more than one juncture is present, the lateral support provided by the multiple junctures 126 may allow the positioning member 102 to be thinner at its lower end 106, which may allow for a reduction in the overall size of the positioning member 102. The junctures 126 may allow for the use of a denser (less compressible) fill material in the positioning member 102. The amount of filler, compactness of filler, and/or firmness of the filler may be reduced with the use of the lateral junctures 126 as compared with the use of a single juncture 126. Any one or more of these reductions may also lead to decreased costs in the manufacture, packaging, and distribution of the head positioning aid 100.

Figure 7:
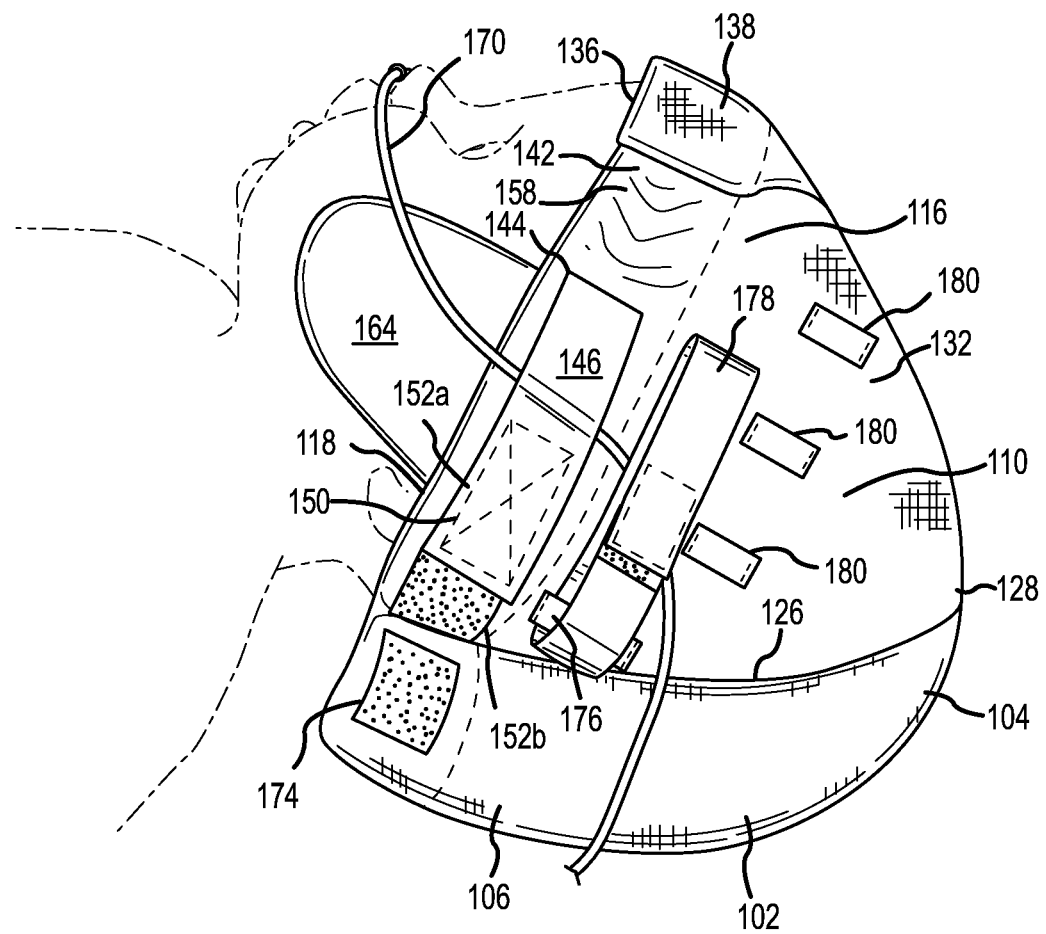
FIG. 7 is a right isometric view of a head positioning aid according to another embodiment applied to an infant's head.

In some implementations, the head positioning aid 100 includes a cheek flap 164. The cheek flap 164 may help protect the skin of an infant's face from abrasion or other damage caused by a medical device, such as a nasal cannula 170, touching or laying on the face. The cheek flap 164 may be any size and shape that helps protect the skin from a medical device. With reference to FIG. 7, the cheek flap 164 may be substantially U-shaped.

The cheek flap 164 may be constructed of any one or more soft fabric materials known in the art. The fabric material may be any material as described above for the headwear member 110. The cheek flap 164 may be constructed of the same fabric material as the headwear member 110, or may be constructed of a different fabric material.

A cheek flap 164 may be positioned between the front opening 136 and a positioning member 102 on the same side of headwear member 110. For example, a cheek flap 164 may be positioned at or near the opening 144 in the hem 158. A cheek flap 164 may be positioned at or near an adjustment member attachment 152b in or on the headwear member 110.

A cheek flap 164 may be permanently or releasably secured to the head positioning aid 100. The cheek flap 164 may be secured to the headwear member 110 by stitches, glue, tape, bonding, fasteners, or any combination thereof. Fasteners may include, for example, buttons, snaps, hook-and-loop fasteners, or hook-and-eye fasteners. As an example, and with reference to FIG. 7, a cheek flap 164 may be secured under the inner surface of the headwear member 110. In other examples, the cheek flap 164 may be secured on top of the outer surface of the headwear member 110 or within the lower portion 116 of the headwear member 110, such as within the hem 158.

When in the down position (see FIG. 7), the cheek flap 164 may lay substantially flat on an infant's face. The cheek flap 164 may lay on part or substantially all of an infant's cheek.

When in the up position (not shown), the cheek flap 164 may lay substantially flat on or under a portion of the headwear member 110. The cheek flap 164 may be releasably secured in the up position by capturing the cheek flap 164 between an adjustment member 146 and the lower portion 116 of the headwear member 110, such as the hem 158. Alternatively, the cheek flap 164 may be secured in the up position by tucking it between the headwear member 110 and the infant's skull.

In the construction and use of a cheek flap 164, its size, shape, material, and position help protect the skin of an infant's face from abrasion and other damage caused by a tube, such as from a nasal cannula, touching or laying on the face.

Figure 5A:
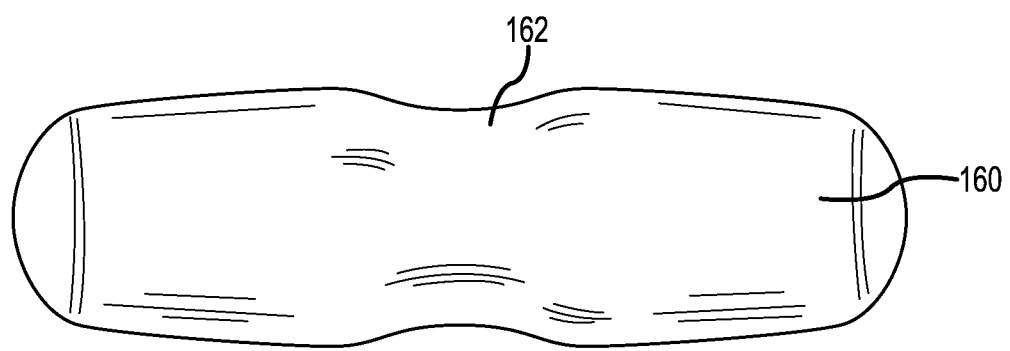
FIG. 5A is a front elevation view of a support member according to one embodiment.
Figure 5B:
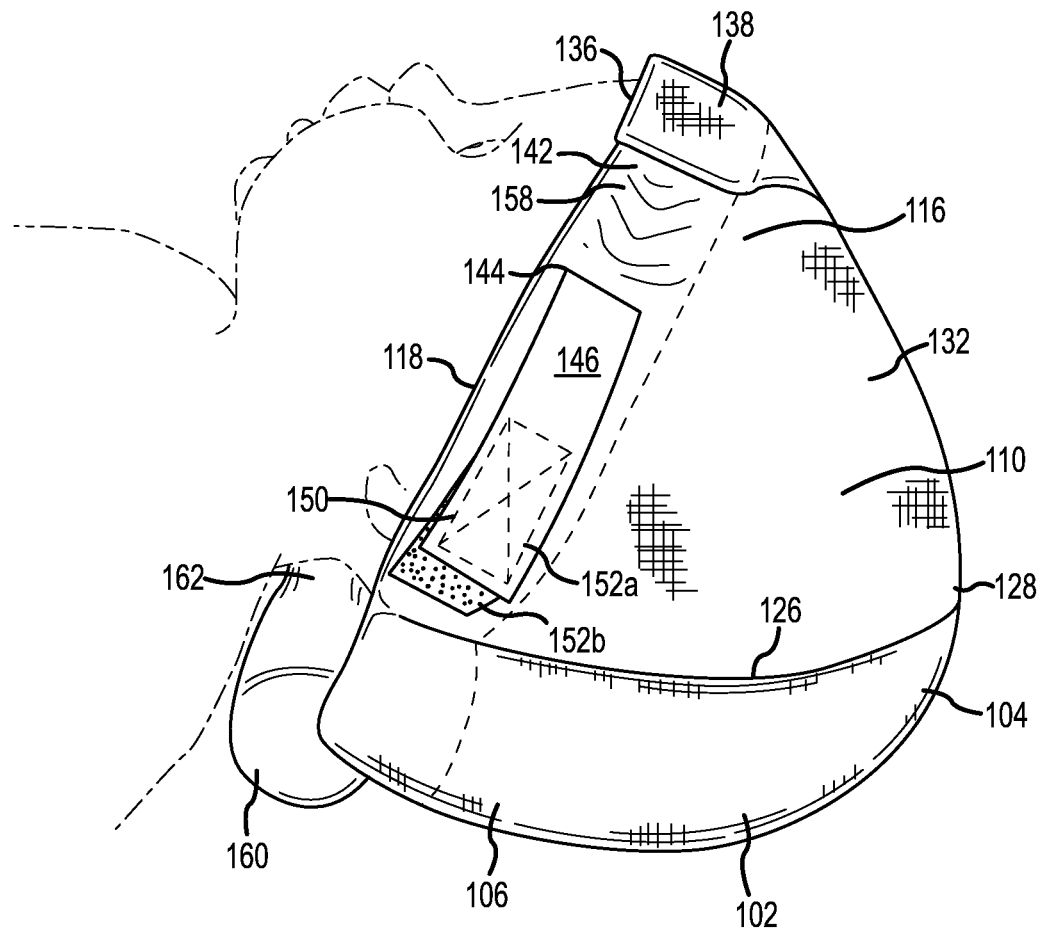
FIG. 5B is a right isometric view of the support member of FIG. 5A used in conjunction with the head positioning aid of FIG. 1 as applied to an infant's head.

In some implementations, the head positioning aid 100 includes a support member 160. With reference to FIGS. 5A and 5B, the support member 160 may be substantially cylindrical in shape. The support member 160 may have a length greater than its width (diameter). The support member 160 may be the same length as, shorter than, or longer than the distance between the lower portions 104 of the positioning members 102. Thus, the support member 160 may extend beyond the lower portion 104 of one or more positioning members 102, extend to the lower portion 104 of one or more positioning members 102, or terminate short of the lower portion 104 of one or more positioning members 102.

A support member 160 may have the same circumference along the entire length of the support member 160, or the circumference may vary along the length of the support member 160. A support member 160 may include a depression 162 at or near the midpoint of its length such that the circumference of the support member 160 is decreased at the depression 162. The depression 162 may be wide enough to accommodate an infant's neck. The depression 162 may be on one or more sides of the support member 160. For example, as show in FIG. 5A, the depression 162 be on all sides of the support member 160 such that it uniformly decreases the circumference of the support member 160.

The support member 160 may be comprised of a filler. The filler may be, for example, solid foam, memory foam, stuffing, batting, down, synthetic down-like material, gel, or a combination thereof. The filler may be resilient such that it returns to its original shape, or close to its original shape, after being compressed. The filler may be of sufficient quantity, compactness, or firmness that it resists complete compression by the weight of an infant's head or neck. The filler may be partially compressible, but has enough compression resistance that it helps the support member 160 support an infant's head or neck. The compression resistance is effective at any weight of an infant's head.

The support member 160 may include a casing, such as a fabric casing. The casing may completely or partially surround the filler. The casing may be constructed with one more seams.

A support member 160 may be physically separate from but used in conjunction with the head positioning aid 100. Alternatively, a support member 160 may be permanently or releasably secured to the head positioning aid 100. The support member 160 may be secured to the back of the lower portion 116 of headwear member 110, such as between the positioning members 102. A headwear member 110 may include a pocket or sleeve into which the support member 160 is placed or removed to releasably secure the support member 160. The support member 160 may be secured to the headwear member 110 by stitches, glue, tape, bonding, fasteners, or any combination thereof. Fasteners may include, for example, buttons, snaps, hook-and-loop fasteners, or hook-and-eye fasteners. By way of example, but not limitation, Velcro may be attached to part or all of the length of a support member 160, and Velcro may be attached to part or all of the hem 158 of the lower portion 116 of the back of the headwear member 110. The support member 160 is thus releasably secured to the headwear member 110 by engaging opposing Velcro pieces.

In the construction and use of a support member 160, its size, shape, compressibility, and attachment to the headwear member 110 help support an infant's head or neck, and help promote an open airway and uniform distribution of respiratory support to the lungs.

Methods of Use of the Head Positioning Aid Comprising Two Positioning Members

By way of example, but not limitation, the head positioning aid 100 of FIGS. 1-4 may be used to support an infant in a midline position according to the following procedure. While the infant is in a supine position, and with the flap 138 in the open position, the head positioning aid 100 may be guided onto the infant's head such that the crown of the head passes through the lower opening 118 until the apex 128 is positioned over the crown of the head. The head positioning aid 100 can be slid down the back of the infant's head, which minimizes disturbance to and stress on the infant. The front opening 136 can be guided over or around any already placed scalp IVs 168, which also minimizes disturbance to and stress on the infant.

The front opening 136 is positioned near the center front of the infant's head. Before the flap 138 is closed, the tubes of any previously placed scalp IVs 168 may be guided out of the front opening 136 to a position away from the infant's face. The flap 136 is then secured to the headwear member 110 by pressing together opposing Velcro-flap attachments 140a, 140b. While the head positioning aid 100 is being worn by an infant, the flap 138 can be opened at any time and the headwear member 110 slid backward to permit easy access to the scalp for placement, removal, or monitoring of scalp IVs 168. The flap 138 can also be partially or completely opened or closed for temperature monitoring, regulation, and stabilization.

The lower portion 116 of the headwear member 110 is positioned such that it rests on or near the forehead, on or near the ears, and on or near the back of the neck. If the headwear member 110 is too big, the circumference of the lower portion 116 is tightened by pulling the free end 150 of each adjustment member 146 from the front opening 136 towards the positioning member 102 on the same side of the headwear member 110 as the adjustment member 146. Pulling on the free ends 150 causes the fabric of the hem 158 that creates the pocket 142 to gather together, thereby decreasing the effective circumference of the lower portion 116. The adjusted size of the headwear member 110 is maintained by pressing together opposing Velcro-adjustment member attachments 152a, 152b. If the headwear member is too tight, it can be loosened by releasing the free end 150, which lets out the gathers in the fabric of the hem 150 that creates the pocket 142, thereby increasing the effective circumference of the lower portion 116. The adjustment member 146 helps fit the headwear member 110 to multiple sizes of infants' heads. The adjustment member 146 also allows the headwear member 110 to be loose when it is applied to an infant's head, which minimizes disturbance to and stress on the infant.

Before the adjustment member attachments 152a, 152b are engaged, a previously placed nasal cannula tube 172 can be guided between the free end 150 of the adjustment member 146 and the opening 144 in the hem 158. When the adjustment member attachments 152a, 152b and engaged, the nasal cannula tube 172 is captured between the adjustment member 146 and the headwear member 110. Securing a nasal cannula tube 172 to the headwear member 110 helps to selectively position the tube 172. Securing a nasal cannula tube 172, or any other similar device, to the headwear member 110 also helps to avoid placing medical tape on an infant's face, which is damaging to the infant's face.

The positioning members 102 are positioned on either side of the infant's head, behind the ears. The positioning members 102 maintain an infant's head in midline and deflect an infant's moving head back to midline. The positioning members 102 follow the curvature of the infant's head such that the lower portions 116 may fall behind or in front of the tops of the shoulders. This arrangement of the lower portions 116 helps provide additional lateral support to the positioning members 102 for maintaining the head in a midline position. When the infant's head rests on or rolls onto a positioning member 102, the positioning member 102 deflects the infant's head back to midline. The shape, thickness, and/or firmness of the positioning members 102 may help to deflect an infant's head back to midline. Maintaining an infant's head in midline helps to promote optimal cerebral blood flow and uniform distribution of respiratory support to the lungs. The positioning members 102 are positioned laterally, which diminishes pressure to the side of the face and head and thereby helps to prevent the development of dolichocephaly.

The head positioning aid 100 of another embodiment, as depicted in FIG. 6, may be used to support an infant in a midline position according to the following procedure. While the infant is in a supine position, and with the slit 154 in the open position, the head positioning aid 100 is guided onto the infant's head such that the crown of the head passes through the lower opening 118 until the apex 128 is positioned over the crown of the head. The head positioning aid 100 can be slid down the back of the infant's head, which minimizes disturbance to and stress on the infant. The front opening 136 can be guided over or around any already placed scalp IVs 168, which also minimizes disturbance to and stress on the infant.

The front opening 136 is positioned near the center front of the infant's head. Before the slit 154 is closed, the tubes of any previously placed scalp IVs 168 are guided out of the front opening 136 to a position away from the infant's face. The sides of the slit 154 are then secured to each other by pressing together opposing Velcro fasteners 156. While the head positioning aid 100 is being worn by an infant, the slit 154 can be opened at any time to permit easy access to the scalp for placement, removal, or monitoring of scalp IVs 168. The slit 154 can also be partially or completely opened or closed for temperature monitoring, regulation, and stabilization.

Use of the head positioning aid of FIG. 6 in all other aspects, such as adjusting the size of the headwear member 110, securing nasal cannula tubes 172, and maintaining an infant's head in midline, are as described above for FIGS. 1-4.

The head positioning aid 100 of another embodiment, as depicted in FIG. 8, may be used to support an infant in a midline position while the infant is lying on its side according to the following procedure. The head positioning aid 100 is guided onto the infant's head and the headwear member is adjusted as described above for FIGS. 1-4.

The front opening 136 is positioned between the center of the forehead and the ear on which the head is not resting. The front opening 136 operates as described above for FIG. 1-4 or 6.

The positioning members 102 are positioned towards the front and back of the infant's head. The infant's head may lie on one or more positioning members 102, or may lie between the positioning members 102. The positioning members 102 support and maintain an infant's head in a midline position while the infant is lying on its side. Supporting and maintaining an infant's head in a midline position helps to reduce pressure to the side of the head between the positioning members 102 and thereby helps to prevent the development of dolichocephaly. The side of the head on which the infant is positioned may be alternated, which also helps to prevent the development of dolichocephaly.

The head positioning aid 100 of the embodiments depicted in FIGS. 1-4, 5B, 6, or 8 may include one or more cheek flaps 164. For example, the head positioning aid 100 of the embodiment depicted in FIGS. 1-4 is shown with a cheek flap 164 in FIG. 7. By way of example, but not limitation, a head positioning aid 100 may be used with one or more cheek flaps 164 to support an infant's head in midline, as well as to protect the skin of the face of an infant, according to the following procedure.

The head positioning aid 100 may be applied to an infant's head according to any of the methods described above. The cheek flap 164 may be positioned in the down position before a medical device, such as a nasal cannula 170, is placed. When the nasal cannula 170 is placed, it is positioned on top of the cheek flap 164 such that the cheek flap 164 is between the nasal cannula tube 172 and the infant's face. Alternatively, the cheek flap 164 may be slid between an already placed nasal cannula tube 172 and an infant's cheek. The check flap 164 helps protect an infant's skin from abrasion or other damage caused by the nasal cannula tube 172.

Additionally, as shown in FIG. 7, the positioning members 102 may be provided with an attachment surface 174 for connection with respective adjustment member attachments 152a/b on either side of the headwear member 110. For example, the attachment surfaces 174 may be made of an opposing side of a hook and loop fasting material as the material of the respective adjustment member attachments 152a/b. In this manner, the positioning members 102 may be held in positions that are further spread apart from each other depending upon the head size of the infant or particular treatment desired.

The head positioning aid 100 may also have a pair of shade loops 178 connected to the headwear member 110 on lateral sides thereof in front of the respective positioning members 102 and above the adjustment members 146. The shade loops 178 may be attached to the headwear member 110 by retention loops 176. The retention loops 176 may be formed of the same or different fabric as the headwear member 110 and may be attached at opposing ends, e.g., by stitching, to the headwear member 110 to form a loop. The shade loops 178 may be formed of a longer length of material, e.g., and elastic material, that has opposing closure structures (e.g., opposing hook and loop fastener material) on each end of the length. Thus, the shade loops 178 may be passed through the retention loops 176 and the ends connected together to form a closed loop that is attached to the headwear member 110. The length and location of the shade loops 178 may be configured to connect with an retain a pair of bilishades in place over the eyes of the infant wearing the head positioning aid 100.

A number of tie-down loops 180 may further be connected to the headwear member 110 as shown in FIG. 7. The tie-down loops 180 may be formed of the same or different fabric as the headwear member 110 and may be attached at opposing ends, e.g., by stitching, to the headwear member 110 to form a loop. The tie-down loops 180 may be place at any number of appropriate or convenient locations on the headwear member 110 to allow for a medical device or tubes or wired connected to a medical device to be tied down, e.g., with ribbon or string ties, and routed away from the face of the infant. In some embodiments, as separate ribbon band with a number of tie-down loops 180 provided thereon may be attached to the headwear member 110 (e.g., across the front thereof) to provide a convenient structure for the provision of multiple tie-down loops 180. It may be noted that the provision of the tie-down loops 180, the shade loops 178, and the adjustment members 146 may allow for the retention and direction of tubes and cables of medical devices and for ease of repositioning the infant without having to remove and replace such tubes and cables as is often the case when such tubes and cables are directly attached to the infant.

The head positioning aid 100 of the embodiments depicted in FIG. 1-4 or 6-8 may also be used to support an infant in a midline position according to the following alternative procedure. An infant is placed on its back or on its side on a flattened head positioning aid 100 (see FIG. 4), or a flattened head positioning aid 100 is guided underneath, but not over, an infant's head. Placing an infant on a flattened head positioning aid 100 or sliding the head positioning aid 100 down the back of the infant's head minimizes disturbance to and stress on the infant. The head positioning aid 100 is positioned with its front side facing the incubator mattress or other surface and with its back side facing the infant's head. The apex 128 of the headwear member 110 is positioned behind the crown of the head. The lower portion 116 of the headwear member 110 is positioned behind the back of the neck. The positioning members 102 are positioned laterally when an infant's head is in a midline supine position. The positioning members 102 are positioned toward the front and back of the head when an infant's head is in midline and the infant is lying on its side. The positioning members 102 maintain the infant's head in midline as described above. The front opening 136, adjustment members 146, and cheek flaps 164 are not utilized in this alternative procedure.

The head positioning aid 100 of the embodiments depicted in FIG. 1-4 or 6-8 may include a support member 160 as depicted in FIG. 5A. For example, the head positioning aid 100 of the embodiment depicted in FIGS. 1-4 is shown with a support member 160 in FIG. 5B. By way of example, but not limitation, a head positioning aid 100 may be used with a support member 160 to support an infant's head in a midline position, as well as to support the neck of an infant and promote an open airway, according to the following procedure.

The head positioning aid 100 may be applied to or behind an infant's head according to any of the methods described above. The support member 160 may already be attached to the headwear member 110, or it may be slid behind the neck of an infant after the head positioning aid 100 has been positioned. The neck of the infant rests on the depression 162 in the support member 160. The support member 160 helps support an infant's head or neck. The support member 160 also helps promote an open airway and uniform distribution of respiratory support to the lungs, such as when an infant is on a ventilator.

The article "a" or "an" preceding a term, as used herein, refers to one or more of that term. As such, the terms "a" or "an", "one or more", and "at least one" should be considered interchangeable herein.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:
1. A device for the treatment and prevention of infant health conditions caused by improper head position comprising a headwear member made of a fabric material sized to fit around an infant's head and comprising overlapping or adjacent portions that define an opening in the headwear member;

two longitudinally-elongated, partially compressible and compression-resistant, head positioning members spaced laterally apart from each other and fixedly attached on an outer surface of the headwear member, wherein an upper end of each head positioning member is at or near an apex of the headwear member and a lower end of each head positioning member is near a lower portion of the headwear member, wherein the head positioning members are configured to minimize movement of the head, thereby maintaining the head in a midline position with respect to the spine of the infant when the infant is supine or lying on its side; and at least two adjustment members configured to releasably secure a medical device to the outer surface of the headwear member, wherein each adjustment member has a fixed end and a free end;

wherein the portions of the headwear member are movable between an open position and a closed position, when in the open position expose the scalp of the infant, and when in the closed position, permit secure attachment of a medical device to the headwear member.

2. A device for the treatment and prevention of infant health conditions caused by improper head position comprising a headwear member made of a fabric material sized to fit around an infant's head and comprising overlapping or adjacent portions that define an opening in the headwear member;

a partially compressible and compression-resistant head positioning member having first and second portions spaced laterally apart from each other allowing a head of an infant to rest therebetween on a surface, wherein each of the first and second portions of the head positioning member is fixedly attached on an outer surface of the headwear member and extends outward from an outer surface of the headwear member, wherein an upper end of each of the first and second portions is at or near an apex of the headwear member and a lower end of each of the first and second portions is near a lower portion of the headwear member, wherein the first and second portions are configured to minimize movement of the head, thereby maintaining the head in a midline position with respect to the spine of the infant when the infant is supine or lying on its side; and at least two adjustment members configured to releasably secure a medical device to the outer surface of the headwear member, wherein each adjustment member has a fixed end and a free end;

wherein the portions of the headwear member are movable between an open position and a closed position, when in the open position expose the scalp of the infant, and when in the closed position, permit secure attachment of a medical device to the headwear member.

3. The device of claim 1, wherein the medical device is selected from a wire, a tube, an IV tube, a cannula, a cable, and a monitoring device.

4. The device of claim 1 further comprising one or more tie-down loops affixed to the surface of the headwear member and configured to retain and direct a medical device or a portion thereof to a desired location.

5. The device of claim 4, wherein the at least one loop is a pair of laterally positioned loops with closures configured to connect to bilishades.

6. The device of claim 2, wherein the first and second portions of the head positioning member further comprise two separate, longitudinally elongated, partially compressible and compression resistant head positioning members spaced laterally apart from each other on a rear surface of the headwear member.

7. The device of claim 2, wherein the medical device is selected from a wire, a tube, an IV tube, a cannula, a cable, and a monitoring device.

8. The device of claim 2 further comprising one or more tie-down loops affixed to the surface of the headwear member and configured to retain and direct a medical device or a portion thereof to a desired location.

9. The device of claim 8, wherein the at least one loop is a pair of laterally positioned loops with closures configured to connect to bilishades.

10. The device of claim 1, wherein the fixed end of each adjustment member is secured at or near a lower portion of the headwear member.

11. The device of claim 2, wherein the fixed end of each adjustment member is secured at or near a lower portion of the headwear member.

* * * * *

UNITED STATES PATENT AND TRADEMARK OFFICE
CERTIFICATE OF CORRECTION

PATENT NO. : 10,980,659 B2
APPLICATION NO. : 14/312594
DATED : April 20, 2021
INVENTOR(S) : Jane Scott et al.

Page 1 of 1

It is certified that error appears in the above-identified patent and that said Letters Patent is hereby corrected as shown below:

In the Claims

Column 21, Line 10, Claim 1, replace "is at or near" with --is attached at or near--;
  Line 11, Claim 1, replace "is near" with --is attached near--;
  Line 43, Claim 2, replace "is at or near" with --is attached at or near--;
  Line 45, Claim 2, replace "is near" with --is attached near--.

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*